(12) United States Patent
Griswold (10) Patent No.: US 8,801,775 B2
(45) Date of Patent: Aug. 12, 2014

(54) HELICAL STENT WITH OPPOSING AND/OR ALTERNATING PITCH ANGLES

(75) Inventor: Erik Griswold, Penngrove, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 716 days.

(21) Appl. No.: 12/768,210

(22) Filed: Apr. 27, 2010

(65) Prior Publication Data

US 2011/0264195 A1 Oct. 27, 2011

(51) Int. Cl.
- *A61F 2/06* (2013.01)
- *A61F 2/88* (2006.01)
- *A61F 2/915* (2013.01)

(52) U.S. Cl.
CPC . *A61F 2/915* (2013.01); *A61F 2/88* (2013.01); *A61F 2002/91558* (2013.01); *A61F 2002/91508* (2013.01)
USPC ...................................................... 623/1.22

(58) Field of Classification Search
USPC ...................................................... 623/1.22
See application file for complete search history.

(56) References Cited

U.S. PATENT DOCUMENTS

| | | | |
|---|---|---|---|
| 4,886,062 A | 12/1989 | Wiktor | |
| 5,135,536 A | 8/1992 | Hillstead | |
| 5,314,472 A | 5/1994 | Fontaine | |
| 5,800,456 A * | 9/1998 | Maeda et al. | 623/1.15 |
| 5,938,697 A * | 8/1999 | Killion et al. | 623/1.15 |
| 6,010,530 A * | 1/2000 | Goicoechea | 623/1.13 |
| 6,273,911 B1 * | 8/2001 | Cox et al. | 623/1.15 |
| 6,319,277 B1 * | 11/2001 | Rudnick et al. | 623/1.13 |
| 6,355,059 B1 * | 3/2002 | Richter et al. | 623/1.17 |
| 6,520,986 B2 | 2/2003 | Martin et al. | |
| 6,551,350 B1 * | 4/2003 | Thornton et al. | 623/1.13 |
| 6,569,193 B1 * | 5/2003 | Cox et al. | 623/1.15 |
| 6,610,086 B1 * | 8/2003 | Kock et al. | 623/1.22 |
| 6,878,162 B2 * | 4/2005 | Bales et al. | 623/1.15 |
| 7,033,386 B2 | 4/2006 | Richter et al. | |
| 7,252,679 B2 | 8/2007 | Fischell et al. | |
| 7,381,217 B2 | 6/2008 | Tischler | |
| 8,366,765 B2 * | 2/2013 | Baldwin et al. | 623/1.22 |
| 2002/0007212 A1 * | 1/2002 | Brown et al. | 623/1.16 |
| 2002/0116044 A1 * | 8/2002 | Cottone et al. | 623/1.2 |
| 2004/0243216 A1 * | 12/2004 | Gregorich | 623/1.15 |
| 2008/0319535 A1 | 12/2008 | Craven et al. | |

FOREIGN PATENT DOCUMENTS

| EP | 565251 | 10/1993 | |
|---|---|---|---|
| EP | 565251 A1 * | 10/1993 | A61M 29/00 |

* cited by examiner

*Primary Examiner* — Paul Prebilic (57) ABSTRACT

Waveforms for forming helical stents with opposing and/or alternating pitch angles along their lengths are disclosed. A wire is bent to form a waveform having a series of sinusoidal segments between a first end and a second end thereof. Each sinusoidal segment is longitudinally offset from its adjacent segment(s). Each waveform includes at least one sinusoidal segment having a first portion in which the amplitude between consecutive turns of the wire gradually increases and a longitudinally offset second portion in which the amplitude between consecutive turns of the wire gradually decreases. The waveform is wrapped from one end to the other about a mandrel to form the stent and depending on the arrangement of sinusoidal segments along the waveform may have opposing and/or alternating pitch angles along a section or an entire length of the stent.

17 Claims, 7 Drawing Sheets

HELICAL STENT WITH OPPOSING AND/OR ALTERNATING PITCH ANGLES

FIELD OF THE INVENTION

The present invention relates generally to stents and methods of making stents, and more particularly, to helical stents.

BACKGROUND OF THE INVENTION

Cardiovascular disease, including atherosclerosis, is the leading cause of death in the United States. The medical community has developed a number of methods and devices for treating coronary heart disease, some of which are specifically designed to treat the complications resulting from atherosclerosis and other forms of coronary arterial narrowing.

One method for treating atherosclerosis and other forms of coronary narrowing is percutaneous transluminal coronary angioplasty, commonly referred to as "angioplasty" or "PTCA". The objective in angioplasty is to enlarge the lumen of the affected coronary artery by radial hydraulic expansion. The procedure is accomplished by inflating a balloon within the narrowed lumen of the coronary artery. Radial expansion of the coronary artery occurs in several different dimensions, and is related to the nature of the plaque. Soft, fatty plaque deposits are flattened by the balloon, while hardened deposits are cracked and split to enlarge the lumen. The wall of the artery itself is also stretched when the balloon is inflated.

Unfortunately while the affected artery can be enlarged, in some instances restenosis of the vessel occurs negating the positive effect of the angioplasty procedure. In the past, such restenosis has frequently necessitated repeat angioplasty or open heart surgery. While such restenosis does not occur in the majority of cases, it occurs frequently enough that such complications comprise a significant percentage of the overall failures of the angioplasty procedure.

To lessen the risk of restenosis, various devices have been proposed for mechanically keeping the affected vessel open after completion of the angioplasty procedure. Such endoprostheses (generally referred to as "stents") are typically inserted into the vessel, positioned across the lesion or stenosis, and then expanded to keep the passageway clear. The stent overcomes the natural tendency of the vessel walls of some patients to restenose, thus maintaining the patency of the vessel.

Stents are delivered to the lesion, or target area, by a catheter. Typically, the stent is percutaneously introduced into the patient in an unexpanded form, having the smallest diameter possible. The small diameter is necessary during insertion in order to facilitate traversing tortuous blood vessels. When the stent reaches the target area, the stent is expanded to engage the blood vessel walls, enlarging the inner circumference of the blood vessel, and supporting the vessel wall.

The stent may be self-expanding or expanded by a number of mechanical methods, including expansion of the stent using a balloon on a balloon catheter. The balloon is inserted into the unexpanded stent, either before insertion into the patient or after the stent has reached the target site. The balloon is inflated while inside the stent, forcing the stent to expand and lodge within the blood vessel at the target site.

Stents are generally formed using any of a number of different methods. One group of stents are formed by winding a wire around a mandrel, welding or otherwise forming the stent to a desired configuration, and finally compressing the stent to an unexpanded diameter. Another group of stents are manufactured by machining tubing or solid stock material into bands, and then deforming and joining the bands to form a desired tubular configuration. Another group of stents are formed by laser etching or chemical etching, which cuts or etches a tube to a desired shape. The stent is usually etched or cut in an unexpanded state.

Helically wound stents, such as those described in U.S. Pat. No. 4,886,062 to Wiktor, the contents of which are incorporated by reference herein, generally comprise a wire formed into a waveform, such as a sinusoid, that is then helically wrapped around a mandrel to provide a tubular or cylindrical structure. Helically wound stents, however, generally include ends that are not substantially perpendicular to the longitudinal axis of the stent. In other words, due to the helical winding of the wire, a portion of each end of the stent extends further longitudinally than the remainder of each end of the stent, as shown in FIG. 2 of the Wiktor patent. In some helically wound stents, such as those described in U.S. Pat. No. 5,314,472 to Fontaine, end portions of the wire have a reduced amplitude waveform as compared to the waveforms in the middle of the wire. Wrapping such a wire around a mandrel to form a stent results in a stent with ends that may be generally perpendicular to the longitudinal axis of the stent.

Helically wound stents require a wrapping pitch or pitch angle to enable subsequent wraps of the waveform to build length of the stent without overlapping. Though the pitch angle may vary in degree of angular inclination along a length of the stent, wrap progression typically requires all pitch angles to be in the same angular direction from a reference line perpendicular to a longitudinal axis of the stent, i.e., the pitch angle(s) is/are inclined to the left of the reference line along the length of the stent or is/are inclined to the right of the reference line along the length of the stent. Having all pitch angles inclined in the same angular direction along the length of the stent may create a bias in the physical properties of the stent, which may subsequently affect the performance of the stent while being delivered and deployed in vivo.

BRIEF SUMMARY OF THE INVENTION

Embodiments hereof are directed to waveforms for forming helical stents with opposing and/or alternating pitch angles along a section or an entire length of the stent. A wire is bent to form a waveform having a series of meandering or generally sinusoidal segments between a first end and a second end thereof. Each sinusoidal segment is longitudinally offset from its adjacent segment(s). Each waveform includes at least one sinusoidal segment having a first portion in which the amplitude between consecutive turns of the wire gradually increases and a longitudinally offset second portion in which the amplitude between consecutive turns of the wire gradually decreases. Turns of the wire within such first and second portions may be described as forming an outline of a truncated triangle, a trapezoid, or an isosceles trapezoid. In another embodiment, a sinusoidal segment may include a portion in which the amplitude between turns remains constant, such that turns of the wire within the portion may be described as forming an outline of a parallelogram.

A waveform in accordance with embodiments hereof is wrapped from one end to the other about a mandrel to form a helical stent, which, depending on the arrangement of sinusoidal segments along the waveform, may have opposing and/or alternating pitch angles along a section or an entire length of the stent.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, where like reference numbers indicate identical or functionally similar elements.

Figure 1:
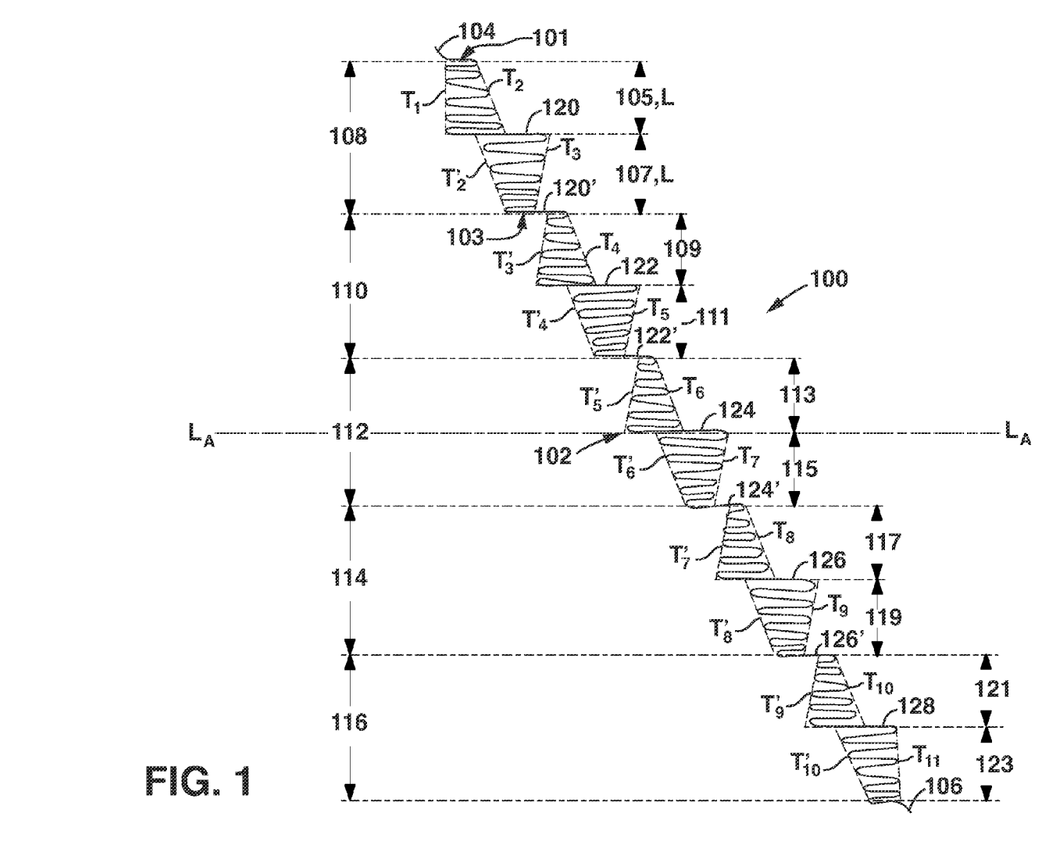
FIG. 1 illustrates a wire bent into a planar waveform for use in making a stent in accordance with an embodiment hereof.
Figure 1A:
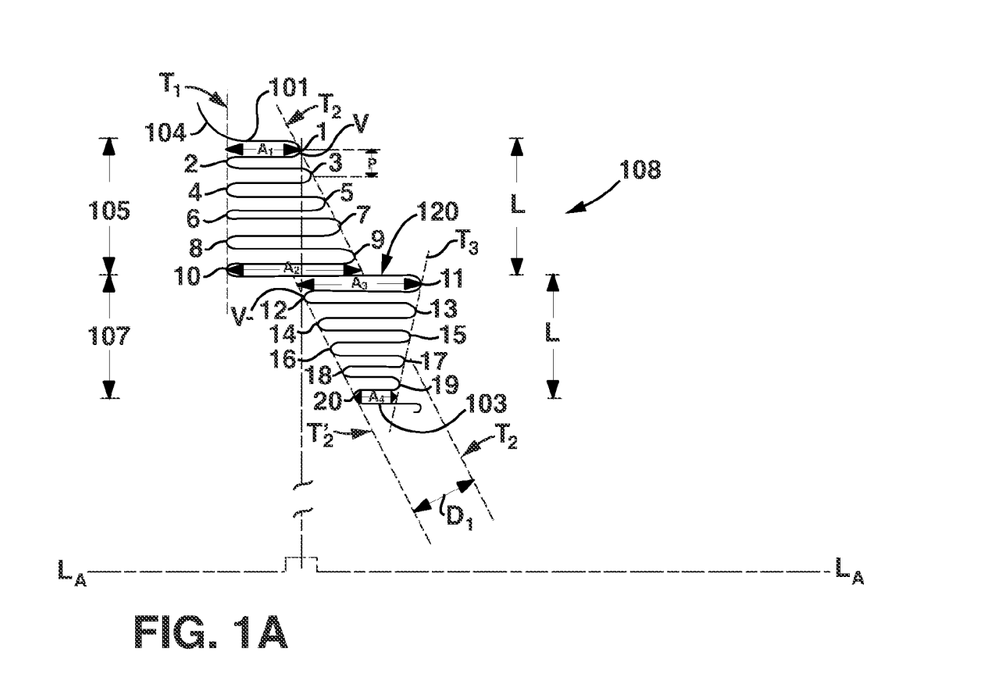
FIG. 1A illustrates an enlarged view of a first sinusoidal segment of the waveform of FIG. 1.
Figure 1B:
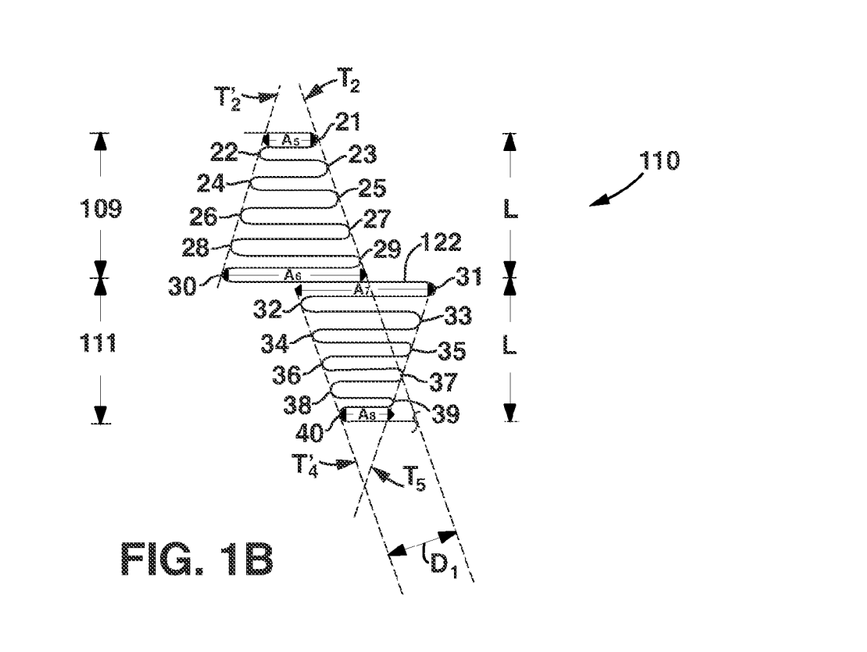
FIG. 1B illustrates an enlarged view of a second sinusoidal segment of the waveform of FIG. 1.

FIG. 1 shows a planar waveform 100 in accordance with an embodiment hereof formed from a wire 102 and FIGS. 1A and 1B are enlarged views of sinusoidal segments 108, 110, respectively, of waveform 100. The term "wire" as used herein means any elongated wire or filament or group of wires or filaments. The wire may be made from any biocompatible material used to form a stent such as stainless steel, nickel-cobalt-chromium-molybdenum "superalloy," titanium-nickel (nitinol), magnesium, steel alloys containing chromium, cobalt, tungsten, and/or iridium, titanium, tantalum, gold, copper or copper alloys, combinations of these materials, or any other biologically compatible low shape-memory material and/or may include composite layers of any of the materials listed. Further, several distinct wires may be twisted together or butt-welded in order to form a continuous wire, or a drawn-filled-tube (DFT) wire may be used wherein a core of a first material is surrounded by a second material. Stents in accordance with embodiments hereof may be either balloon expandable or self-expanding depending on the stent material selected for the wire used to form the waveform and or subsequent processing steps utilized during stent formation as would be understood by one of ordinary skill in the art of stent design.

Although the description of the invention refers to the use of wire to make a waveform that is helically wound into a tubular stent, the invention is not limited to this method of construction. The desired stent pattern having opposing or alternating pitch angles as described herein can be constructed by other known techniques such as removing material from a metal tube to leave the desired pattern. The desired stent pattern can also be formed in a flat sheet that can then be rolled into a cylinder and welded to maintain the tubular shape. In another method, the desired waveform pattern can be formed by removing material from an elongate strip that can then be wrapped to form a helical stent. Methods of removing material to leave a desired stent pattern are well known to those of skill in the field of stent design and may include stamping, laser or chemical etching, and water jet cutting.

Wire 102 forms a series of generally sinusoidal segments 108, 110, 112, 114, 116 between a first end 104 and a second end 106 thereof, wherein each of the segments is longitudinally offset from its adjacent segment(s). Generally the sinusoid formed within each segment 108, 110, 112, 114, 116 includes a first portion 105, 109, 113, 117, 121, respectively, with a gradually increasing amplitude between consecutive turns and a longitudinally offset second portion 107, 111, 115, 119, 123, respectively, with a gradually decreasing amplitude between consecutive turns. Spatially adjacent turns of wire 102 within first portions 105, 109, 113, 117, 121 and second portions 107, 111, 115, 119, 123 form an outline of a truncated triangle. First portion 105 and second portion 123 may more particularly be described as having an outline of a right trapezoid to form opposing ends 230, 232 of a stent 250 that are substantially square to the stent longitudinal axis $L_A$, as described further below. First portions 109, 113, 117, 121 and second portions 107, 111, 115, 119 may more particularly be described as having an outline of an isosceles trapezoid. In each sinusoidal segment, a last turn of the wire in the first portion precedes an opposing first turn of the wire in the second portion with the subsequent consecutive turn of the wire in the second portion occurring such that a vertex thereof substantially aligns along a perpendicular line dropped from a vertex of a corresponding opposing first turn of the first portion to the longitudinal axis $L_A$ as described further below. In this manner, the second portion may be considered to be longitudinally offset from but not longitudinally spaced from the first portion.

Figure 2:
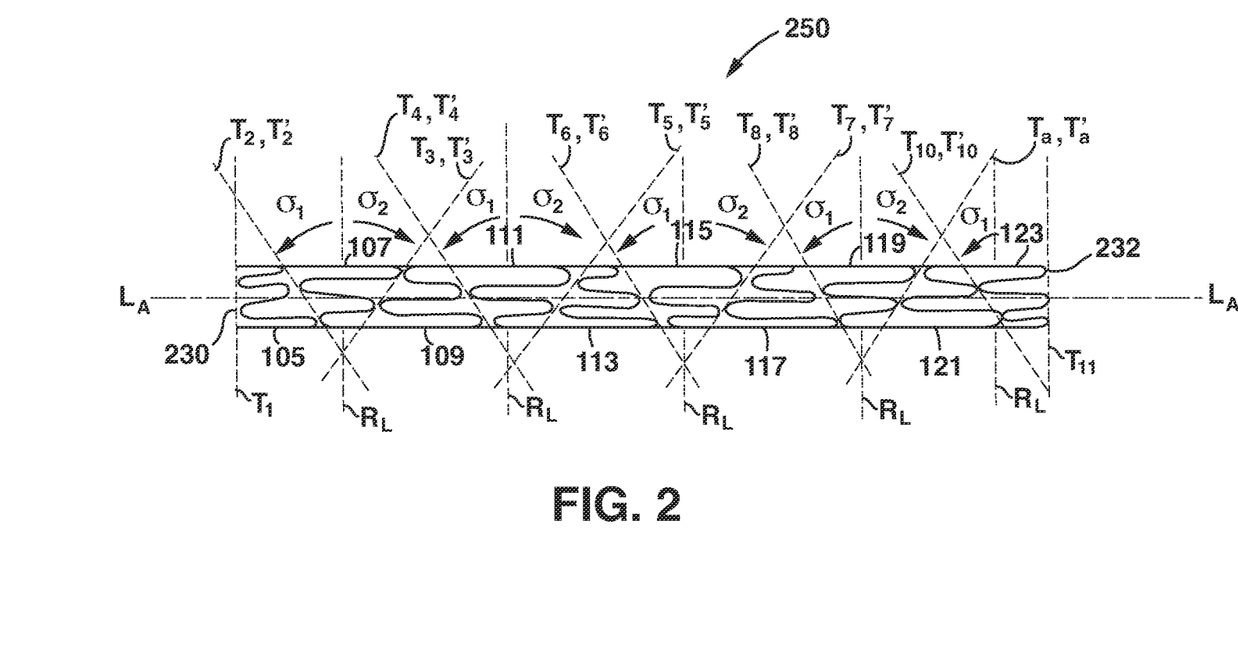
FIG. 2 illustrates a side view of a stent formed from the waveform of FIG. 1 having alternating and opposing pitch angles.

Stent 250, shown in FIG. 2, is formed by wrapping waveform 100 about a mandrel (not shown) starting from either first or second end 104, 106 and proceeding to the opposing end. The diameter of stent 250 illustrated in FIG. 2 is the as-wound diameter, which is a convenient size for fabricating the stent. The as-wound diameter is larger than the compressed or crimped diameter when stent 250 is loaded onto/into a catheter, and is smaller than the nominal expanded diameter when stent 250 is deployed against a vessel wall. Welds (not shown) may be used to connect selected adjacent turns or bends together as will be appreciated by those of ordinary skill in the field of stents. First and fifth sinusoidal segments 108, 116 define opposing end sections of stent 250 with second, third and fourth sinusoidal segments 110, 112, 114 defining body sections of stent 250. In another embodiment, more or fewer body sections may be used to build on or reduce an overall length of stent 250. First portions 105, 109, 113, 117, 121 and second portions 107, 111, 115, 119, 123 are each of a length L, wherein length L is substantially equal to a circumference of stent 250. In another embodiment, each the first and second portions of sinusoidal segments in accordance herewith may be made longer or shorter in order to increase or decrease an outer/inner diameter of stent 250.

Amplitude as used herein means a distance between consecutive turns of the sinusoidal wire, such as representative amplitudes $A_1$, $A_2$, $A_3$ and $A_4$ shown in FIG. 1A. Period as used herein means a distance between adjacent turns of the sinusoidal wire as represented by period P in FIG. 1A. The period may be substantially constant or varied for waveforms made in accordance with embodiments hereof. First sinusoidal segment 108 includes first portion 105 that has an amplitude that gradually increases from amplitude $A_1$ (measured between turns 1, 2) to amplitude $A_2$ (measured between turns 9, 10) along a length L thereof and second portion 107 that has an amplitude that gradually decreases from amplitude $A_3$ (measured between turns 11, 12) to amplitude $A_4$ (measured between turns 19, 20) along a length L thereof, wherein amplitude $A_2$ is substantially equal to amplitude $A_3$. Second portion 107 is longitudinally offset from first portion 105 by a longitudinally extended span 120 of wire 102 that extends from the last turn 10 in first portion 105 to the first turn 11 in second portion 107, with a vertex V' of subsequent consecutive turn 12 in second portion 107 being made to substantially align along a perpendicular line drawn to the longitudinal axis $L_A$ from a vertex V of corresponding opposing first turn 1 of first portion 105. As used herein, corresponding opposing turns refers to two turns of the waveform that lie next to or adjacent each other when the waveform is wrapped into the stent to permit selectively forming turn-to-turn connections. Accordingly in sinusoidal segment 108, turns 3 and 14, turns 5 and 16, turns 7 and 18 and turns 9 and 20 align in a similar manner as turns 1 and 12 to be corresponding opposing turns in accordance herewith.

First portion 105 of sinusoidal segment 108 has turns 2, 4, 6, 8, 10 of wire 102 that align in such a manner that a tangent line $T_1$ (shown dashed) touching turns 2, 4, 6, 8, is perpendicular to a longitudinal axis $L_A$ of a stent 250, which is formed by wrapping waveform 100 as shown in FIG. 2. First portion 105 also has serial turns 1, 3, 5, 7, 9 of wire 102 that align in such a manner that a tangent line $T_2$ (shown dashed) touching turns 1, 3, 5, 7, 9 is at an angle $\sigma_1$ measured from a reference line $R_L$ that is perpendicular to longitudinal axis $L_A$ of stent 250 as shown in FIG. 2. Angle $\sigma_1$ may be selected from a range of values centered on approximately 45 degrees.

Second portion 107 of sinusoidal segment 108 has serial turns 12, 14, 16, 18, 20 of wire 102 aligned in such a manner that a tangent line $T_2'$ (shown dashed) touching turns 12, 14, 16, 18, 20 is substantially parallel to tangent $T_2$ touching turns 1, 3, 5, 7, 9 of first portion 105. Tangent $T_2'$ is spaced a distance $D_1$ from tangent $T_2$ to be generally coincident therewith when waveform 100 is wrapped into stent 250 as shown in FIG. 2. In such an arrangement, when first sinusoidal segment 108 of waveform 100 is wound into stent 250, turns 1, 3, 5, 7, 9 of first portion 105 are located adjacent or proximate to turns 12, 14, 16, 18, 20 respectively of second portion 107, thus providing for selective connections therebetween. Tangent $T_2'$ touching aligned turns 12, 14, 16, 18, 20 of second portion 107 is therefore also at angle $\sigma_1$ to reference line $R_L$. In an embodiment, distance $D_1$ between tangent $T_2$ and tangent $T_2'$ is equal to a width of narrow end portions 101, 103 of first sinusoidal segment 108.

In wrapped stent 250, second portion 107 of sinusoidal segment 108 has serial turns 11, 13, 15, 17, 19 that align in such a manner that a tangent line $T_3$ (shown dashed) touching turns 11, 13, 15, 17, 19 is at an angle $\sigma_2$ measured from reference line $R_L$ on an opposite side thereof from angle $\sigma_1$ to extend in an opposing angular direction therefrom. Angle $\sigma_2$ may be selected from a range of values centered on approximately 45 degrees. Thus angle $\sigma_1$ and angle $\sigma_2$, which are the wrapping pitches or pitch angles of first sinusoidal segment 108 of waveform 100, change angular direction when waveform 100 is wrapped into stent 250.

Second sinusoidal segment 110 is longitudinally offset from first sinusoidal segment 108 by longitudinally extended span 120' of wire 102 that extends from the last turn 20 in second portion 107 (FIG. 1A) to the first turn 21 in first portion 109 (FIG. 1B), with subsequent consecutive turns 21, 22 of wire 102 in first portion 109 being made such there is a longitudinal gap or space between first and second sinusoidal segments 108, 110. Further, extended span 120' is substantially equal to or greater than the sum of amplitude $A_4$ of first segment 108 and amplitude $A_5$ of second segment 110, which is discussed next. As shown in FIG. 1B, second sinusoidal segment 110 includes first portion 109 that has an amplitude between consecutive turns that gradually increases from amplitude $A_5$ (measured between turns 21, 22) to amplitude $A_6$ (measured between turns 29, 30) and a second portion 111 that has an amplitude between consecutive turns that gradually decreases from amplitude $A_7$ (measured between turns 31, 32) to amplitude $A_8$ (measured between turns 39, 40), wherein amplitudes $A_5$ and $A_8$ are substantially equal and amplitudes $A_6$ and $A_7$ are substantially equal. Second portion 111 is longitudinally offset from first portion 109 by a longitudinally extended span 122 of wire 102 that extends from the last turn 30 of wire 102 in first portion 109 to the first turn 31 of wire 102 in second portion 111, with subsequent consecutive turn 32 of second portion 111 being made to align with corresponding opposing turn 21 of first portion 109 as similarly described above with reference to corresponding opposing turns 1, 12 of sinusoidal segment 108.

As shown in FIG. 1B, first portion 109 of sinusoidal segment 110 has turns 22, 24, 26, 28, 30 of wire 102 that align in such a manner that a tangent line $T_3'$ (shown dashed) touching turns 22, 24, 26, 28, 30 is parallel to tangent $T_3$ touching turns 11, 13, 15, 17, 19 of second portion 107 of first sinusoidal segment 108 and is substantially coincident therewith when waveform 100 is wrapped into stent 250 as shown in FIG. 2. In such an arrangement, serial turns 11, 13, 15, 17, 19 of second portion 107 are adjacent to turns 22, 24, 26, 28, 30 respectively of first portion 109 when first and second sinusoidal segments 108, 110 of waveform 100 are wound into stent 250. Similar to tangent $T_3$, tangent $T_3'$ touching turns 22, 24, 26, 28, 30 is at an angle $\sigma_2$ from reference line $R_L$, in an opposing angular direction from angle $\sigma_1$. First portion 109 of sinusoidal segment 111 also has serial turns 21, 23, 25, 27, 29 of wire 102 that align in such a manner that a tangent $T_4$ (shown dashed) touching opposing turns 21, 23, 25, 27, 29 is at an angle $\sigma_1$ measured from a reference line $R_L$, as shown in FIG. 2.

Second portion 111 of sinusoidal segment 110 has serial turns 32, 34, 36, 38, 40 of wire 102 that align in such a manner that a tangent line $T_4'$ (shown dashed) touching turns 32, 34, 36, 38, 40 is parallel to tangent $T_4$ touching turns 21, 23, 25, 27, 29 of first portion 109 and is spaced a distance $D_1$ from tangent $T_4$ to be substantially coincident therewith when waveform 100 is wrapped into stent 250 as shown in FIG. 2. In such an arrangement, turns 21, 23, 25, 27, 29 of first portion 109 are adjacent to turns 32, 34, 36, 38, 40 respectively of second portion 111 when second sinusoidal segment 110 of waveform 100 is wound into stent 250. Tangent $T_4'$ touching aligned turns 32, 34, 36, 38, 40 of second portion 111 is therefore also at angle $\sigma_1$ to reference line $R_L$.

Second portion 111 of sinusoidal segment 110 has serial turns 31, 33, 35, 37, 39 that align in such a manner that a tangent line $T_5$ (shown dashed) touching turns 31, 33, 35, 37, 39 is at an angle $\sigma_2$ from reference line $R_L$ on an opposite side thereof from angle $\sigma_1$ to extend in an opposing angular direction therefrom. Thus angle $\sigma_1$ and angle $\sigma_2$, which are the pitch angles of second sinusoidal segment 110 of waveform 100, change angular direction when waveform 100 is wrapped into stent 250. This change in pitch angles for sinusoidal segment 110 is similar to the change in pitch angles when sinusoidal segment 108 is wrapped into stent 250.

Third sinusoidal segment 112 is longitudinally offset from second sinusoidal segment 110 and fourth sinusoidal segment 114 is longitudinally offset from third sinusoidal segment 112 by respective longitudinally extended spans 122', 124' of wire 102 in a manner as described above with reference to the longitudinal offset between first and second sinusoidal segments 108, 110. Third and fourth sinusoidal segments 112 and 114 share the same sinusoidal pattern as second sinusoidal segment 110, wherein wire 102 in first portions 113, 117, respectively, is bent to have the same gradually increasing amplitude between consecutive turns as first portion 109 and wherein wire 102 in second portions 115, 119, respectively, is bent to have the same gradually decreasing amplitude between consecutive turns of second portion 111. In third and fourth sinusoidal segments 112, 114, second portions 115, 119 are offset from respective first portions 113, 117 by longitudinally extended spans 124, 126 of wire 102 in a manner as previously described with reference to the first and second sinusoidal segments 108, 110. As similarly described in more detail above with reference to second sinusoidal segment 110, turns of third and fourth sinusoidal segments 112 and 114 align with one of respective tangents $T_5'$, $T_6$, $T_6'$, $T_7$, $T_7'$, $T_8$, $T_8'$, and $T_9$ as shown in FIG. 1. When waveform 100 is wrapped to form stent 250 as shown in FIG. 2: turns along tangent $T_5'$ of third sinusoidal segment first portion 113 lie adjacent to turns aligned on tangent $T_5$ of second sinusoidal segment second portion 111; turns aligned on tangent $T_6$ of third sinusoidal segment first portion 113 lie adjacent to turns aligned on tangent $T_6'$ of third sinusoidal segment second portion 115; turns aligned on tangent $T_7'$ of fourth sinusoidal segment first portion 117 lie adjacent to turns aligned on tangent $T_7$ of third sinusoidal segment second portion 115; and turns aligned on tangent $T_8$ of fourth sinusoidal segment first portion 117 lie adjacent to turns aligned on tangent $T_8'$ of fourth sinusoidal segment second portion 119.

Fifth sinusoidal segment 116 is longitudinally offset from fourth sinusoidal segment 114 by longitudinally extended span 126' of wire 102 in a manner as described above with reference to the longitudinal offset between first and second sinusoidal segments 108, 110. First portion 121 of fifth sinusoidal segment 116 shares the same sinusoidal pattern as first portion 109 of second sinusoidal segment 110, wherein wire 102 in first portion 121 has the same gradually increasing amplitude between consecutive turns as first portion 109. Second portion 123 of fifth sinusoidal segment 116 is also offset from first portion 121 by longitudinally extended span 128 of wire 102 in a manner as previously described with reference to first sinusoidal segment 108. When waveform 100 is wrapped to form stent 250, turns aligned on tangent $T_9'$ of fifth sinusoidal segment first portion 121 lie adjacent to turns aligned on tangent $T_9$ of fourth sinusoidal segment second portion 119 and turns aligned on tangent $T_{10}$ of fifth sinusoidal segment first portion 121 lie adjacent to turns aligned on tangent $T_{10}'$ of fifth sinusoidal segment second portion 123. Similar to turns aligned on tangent $T_1$ in first sinusoidal segment first portion 105 that define a squared end 230 of stent 250, fifth sinusoidal segment second portion 123 has a gradually decreasing amplitude with turns thereof aligned in such a manner that a tangent $T_{11}$ (shown dashed) touching the turns is substantially perpendicular to the longitudinal axis $L_4$ of stent 250 to define an opposing squared end 232 of stent 250.

It should be understood from the foregoing that tangents $T_6$, $T_6'$, $T_8$, $T_8'$, $T_{10}$ and $T_{10}'$ are at angle $\sigma_1$ measured from reference lines $R_L$ that are perpendicular to the longitudinal axis $L_4$ of stent 250 and that tangents $T_5'$, $T_7$, $T_7'$, $T_9$ and $T_9'$ are at an angle $\sigma_2$ measured from reference lines $R_L$ on an opposite side thereof from angle $\sigma_1$ to extend in an opposing angular direction therefrom. Thus angles $\sigma_1$ and angles $\sigma_2$, which are the pitch angles of sinusoidal segments 112, 114, 116 of waveform 100, change angular direction when waveform 100 is wrapped into stent 250. Accordingly, stent 250 has alternating and opposing pitch angles $\sigma_1$, $\sigma_2$ along its entire length from end 230 to opposing end 232 such that physical properties, such as flexibility of the stent are consistent along the entire length of the stent. The pattern of alternating and opposing pitch angles $\sigma_1$, $\sigma_2$ balances the load and force distribution to provide substantially consistent and symmetrical gapping as the radially compressed stent is flexed and bent during tracking through tortuous vascular anatomy. The inventive stent thus avoids a problem found in helical stents having constant or near-constant pitch angles, wherein the stent flexibility has a bias typically towards the direction of the pitch progression that can lead to undesirable tracking behavior such as twisting and segment prolapse.

Figure 3:
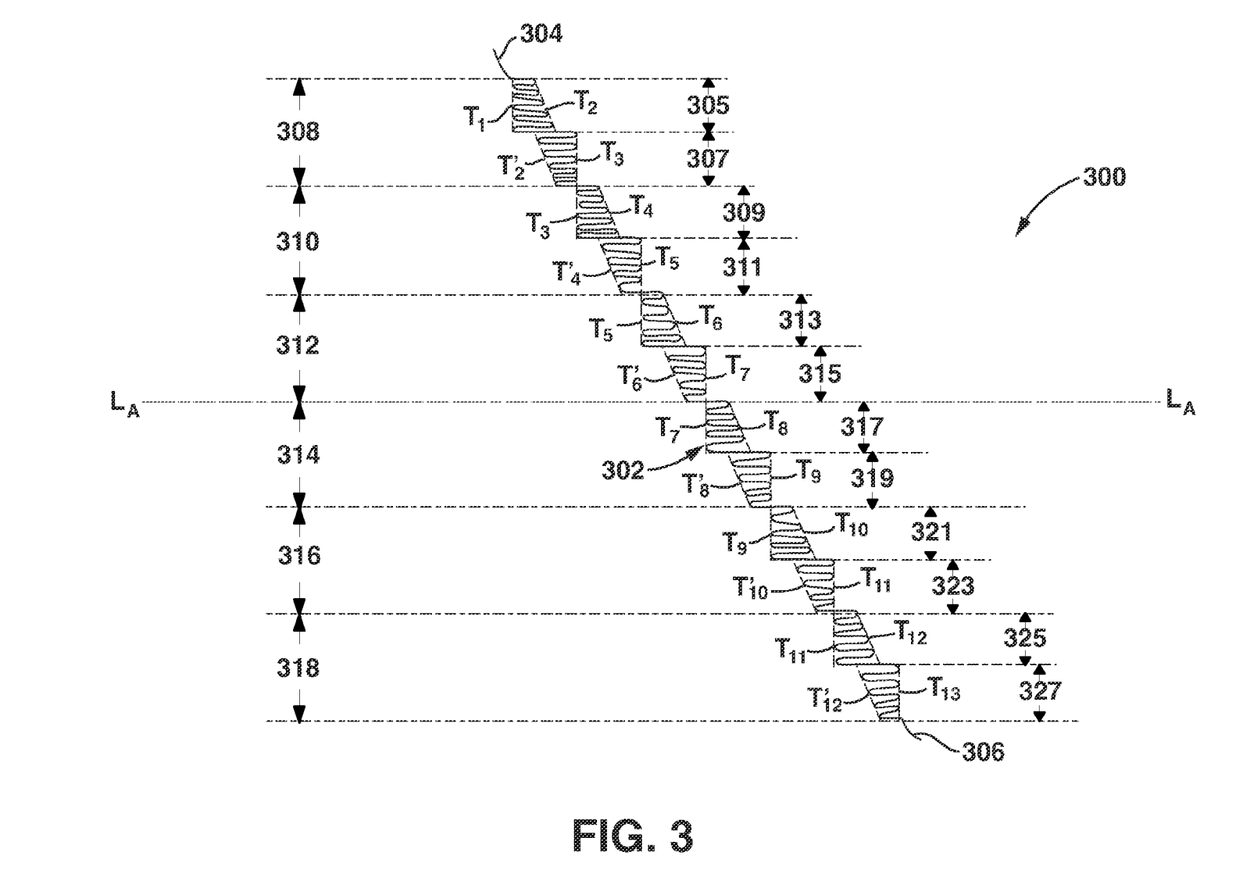
FIG. 3 illustrates a wire bent into a planar waveform for use in making a stent in accordance with another embodiment hereof.
Figure 4:
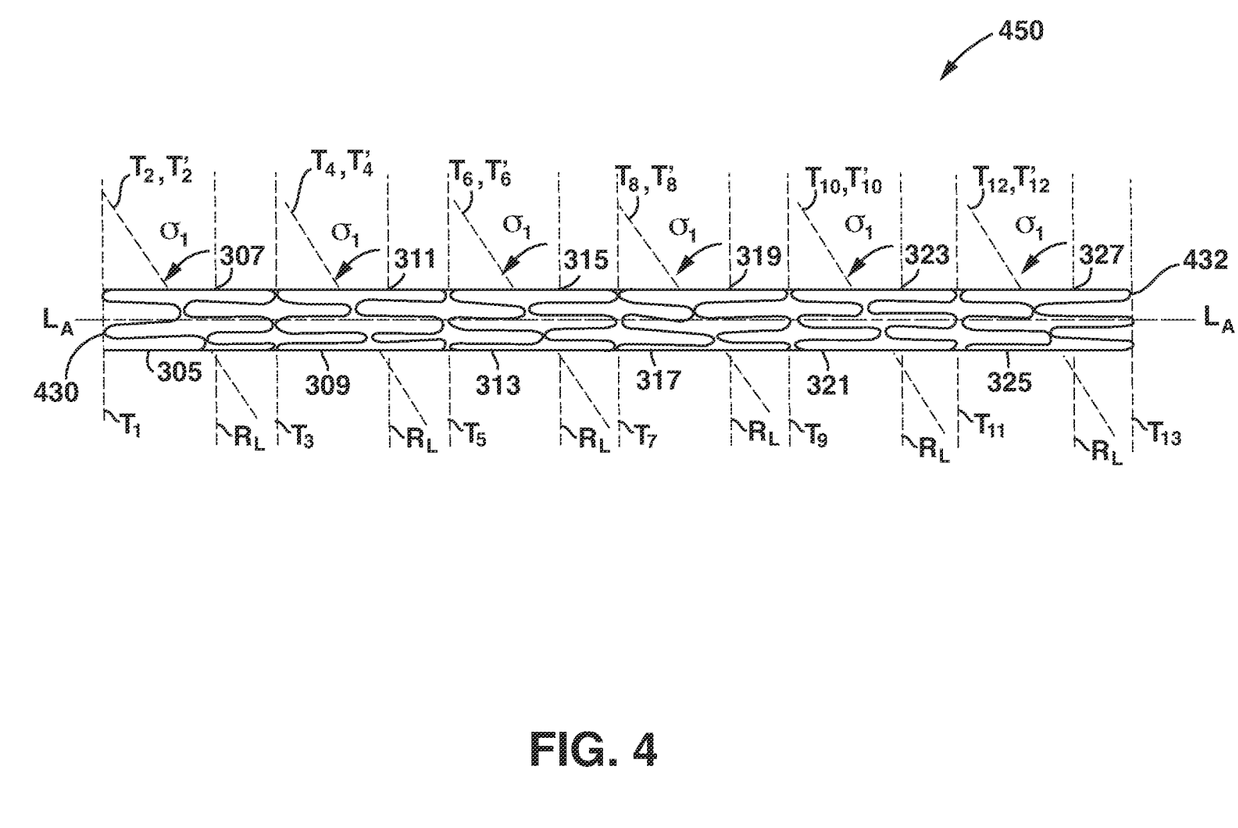
FIG. 4 illustrates a side view of a stent formed from the waveform of FIG. 3 having alternating pitch angles.

FIG. 3 illustrates wire 302 bent into planar waveform 300 in accordance with another embodiment hereof and FIG. 4 illustrates stent 450 formed from waveform 300 of FIG. 3. Wire 302 forms a series of sinusoidal segments 308, 310, 312, 314, 316, 318 between first end 304 and second end 306 thereof, wherein each of the segments is longitudinally offset from an adjacent segment(s). As in the previous embodiment, the sinusoid formed within each segment 308, 310, 312, 314, 316, 318 includes a first portion 305, 309, 313, 317, 321, 325, respectively, with a gradually increasing amplitude between consecutive turns and a longitudinally offset second portion 307, 311, 315, 319, 323, 327, respectively, with a gradually decreasing amplitude between consecutive turns. Physically adjacent turns of wire 302 within first portions 305, 309, 313, 317, 321, 325 and second portions 307, 311, 315, 319, 323, 327 form an outline of a right trapezoid, wherein a longitudinally extended span of wire extends from the last turn in each first portion to an opposing first turn in the respective second portion with the next consecutive turn of the wire in the respective second portion being made at or near a midpoint of a "base" of the first portion. First portion 305 and second portion 327 form opposing substantially squared ends 430, 432 of stent 450.

Stent 450, shown in FIG. 4, is formed by wrapping waveform 300 about a mandrel (not shown) starting from either first or second end 304, 306 and proceeding to the opposing end. Welds (not shown) may be used to selectively connect adjacent turns or bends together. First and last sinusoidal segments 308, 318 define opposing end sections of stent 450 with second, third, fourth and fifth sinusoidal segments 310, 312, 314, 316 defining body sections of stent 450. In another embodiment, more or fewer body sections may be used to build on or reduce an overall length of stent 450. First portions 305, 309, 313, 317, 321, 325 and second portions 307, 311, 315, 319, 323, 327 are each of a length L, wherein length L is substantially equal to a circumference of stent 450. In another embodiment, each of first and second portions of sinusoidal segments in accordance herewith may be made longer or shorter in order to increase or decrease an outer/inner diameter of stent 450.

Each of first portions 305, 309, 313, 317, 321, 325 of sinusoidal segments 308, 310, 312, 314, 316, 318 respectively is identical to first portion 105 of first sinusoidal segment 108, which is described in detail above. First portions 305, 309, 313, 317, 321, 325 each have respective turns of wire 302 that align in such a manner that a respective tangent $T_1$, $T_3$, $T_5$, $T_7$, $T_9$, $T_{11}$ (shown dashed) touching those turns is perpendicular to longitudinal axis $L_4$ of stent 450. Similarly, each of second portions 307, 311, 315, 319, 323, 327 of sinusoidal segments 308, 310, 312, 314, 316, 318 respectively is identical to second portion 123 of fifth sinusoidal segment 116, which is described in detail above. Second portions 307, 311, 315, 319, 323, 327 each have respective turns of wire 302 that align in such a manner that a respective tangent $T_3$, $T_5$, $T_7$, $T_9$, $T_{11}$, $T_{13}$ (shown dashed) touching those turns is perpendicular to longitudinal axis $L_A$ of stent 450. Adjacent sinusoidal segments 308, 310, 312, 314, 316, 318 are longitudinally offset but not longitudinally spaced from one and other, such that tangents $T_3$, $T_5$, $T_7$, $T_9$, $T_{11}$ are common to opposing turns of adjacent first and second portions of adjacent sinusoidal segments such that between longitudinally offset sinusoidal segments 308, 310, e.g., a longitudinally extended span of wire 302 extends from a last turn in second portion 307 to a first turn in first portion 309 with a subsequent consecutive turn of wire 302 in first portion 309 being made to substantially align with the turns of second portion 307 that are touched by tangent $T_3$. The same longitudinal offset is made between all adjacent sinusoidal segments of waveform 300, i.e., where segment 310 transitions to segment 312, where segment 312 transitions to segment 314, where segment 314 transitions to segment 316 and where segment 316 transitions to segment 318.

First portions 305, 309, 313, 317, 321, 325 of sinusoidal segments 308, 310, 312, 314, 316, 318 each also have respective turns of wire 302 that align in such a manner that a respective tangent $T_2$, $T_4$, $T_6$, $T_8$, $T_{10}$, $T_{12}$ (shown dashed) touching those turns is at an angle $\sigma_1$ measured from a reference line $R_L$ that is perpendicular to longitudinal axis $L_A$ of stent 450. Second portions 307, 311, 315, 319, 323, 327 of sinusoidal segments 308, 310, 312, 314, 316, 318, respectively, each also have turns of wire 302 that align in such a manner that a tangent $T_2'$, $T_4'$, $T_6'$, $T_8'$, $T_{10}'$, $T_{12}'$ (shown dashed) touching those turns is parallel to a respective tangent $T_2$, $T_4$, $T_6$, $T_8$, $T_{10}$, $T_{12}$ touching serial turns of respective first portions 305, 309, 313, 317, 321, 325. When waveform 300 is wound into stent 450 as shown in FIG. 4, each tangent $T_2'$, $T_4'$, $T_6'$, $T_8'$, $T_{10}'$, $T_{12}'$ is substantially coincident with a corresponding tangent $T_2$, $T_4$, $T_6$, $T_8$, $T_{10}$, $T_{12}$ such that the turns of the respective first portion aligned on tangent $T_2$, $T_4$, $T_6$, $T_8$, $T_{10}$, $T_{12}$ are adjacent to corresponding turns aligned on tangent $T_2'$, $T_4'$, $T_6'$, $T_8'$, $T_{10}'$, $T_{12}'$ of the respective second portion when the sinusoidal segments 308, 310, 312, 314, 316, 318 are wrapped into stent 450. Thus each of tangents $T_2'$, $T_4'$, $T_6'$, $T_8'$, $T_{10}'$, $T_{12}'$ touching the aligned turns of the second portions is also at angle $\sigma_1$ to reference line $R_L$.

Accordingly, stent 450 has a pitch angle that alternates from squared end 430 to opposing squared end 432 between angle $\sigma_1$ and 0° (as represented by tangents $T_3$, $T_5$, $T_7$, $T_9$, $T_{11}$) relative to reference line $R_L$, whereby physical properties, such as flexibility, of the stent are consistent along the entire length of the stent, as described above with respect to stent 250.

Figure 5:
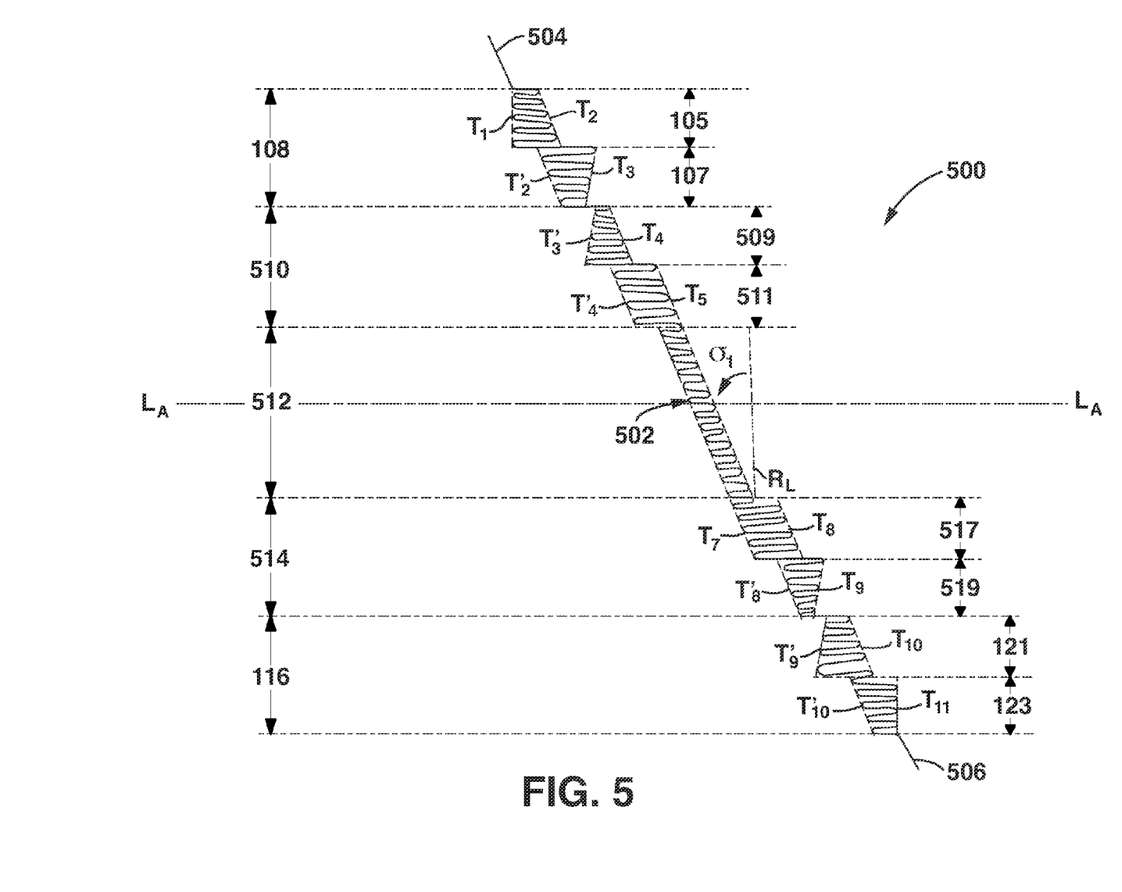
FIG. 5 illustrates a wire bent into a planar waveform for use in making a stent in accordance with another embodiment hereof.
Figure 6:
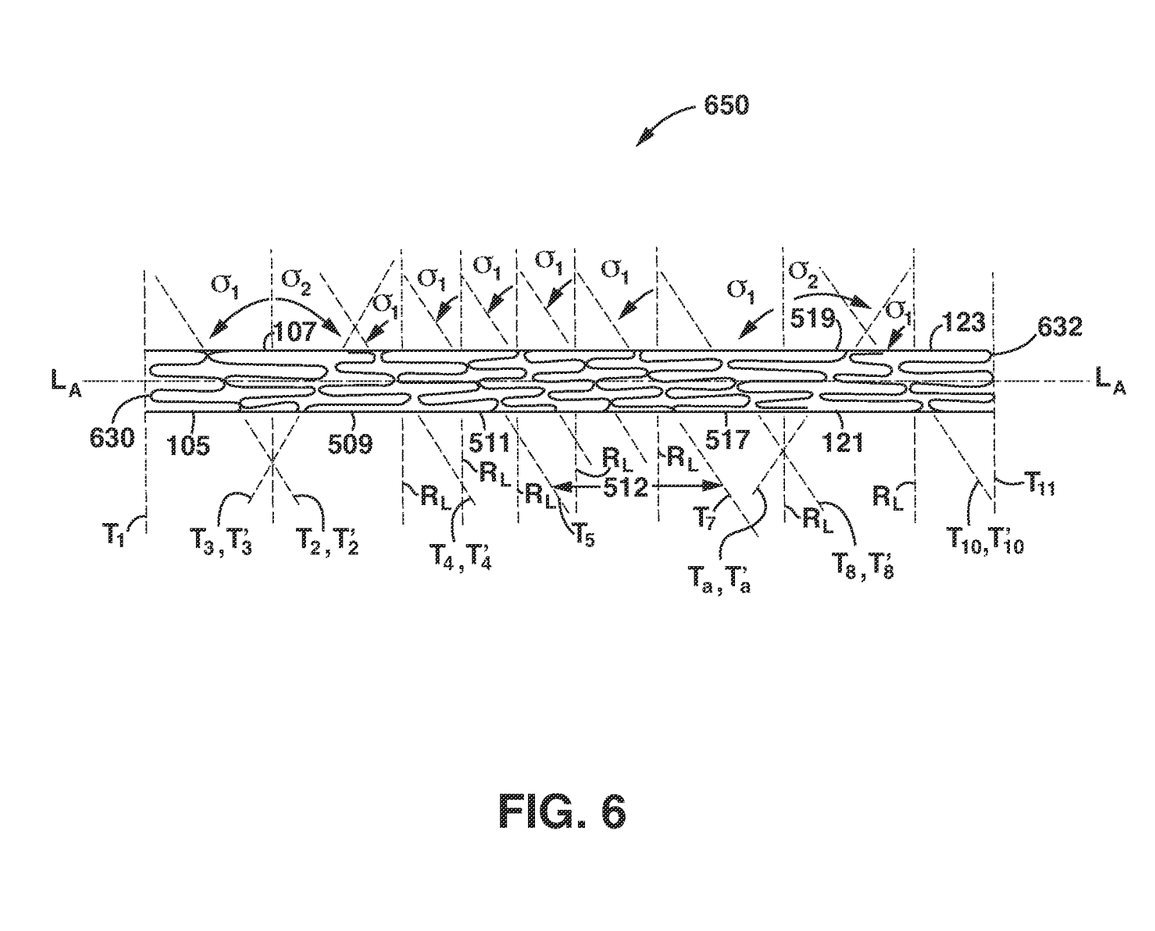
FIG. 6 illustrates a side view of a stent formed from the waveform of FIG. 5.

FIG. 5 illustrates wire 502 bent into planar waveform 500 in accordance with another embodiment hereof and FIG. 6 illustrates stent 650 formed from waveform 500 of FIG. 5. Wire 502 forms a series of sinusoidal segments 108, 510, 512, 514, 116 between first end 504 and second end 506 thereof, wherein each of the segments is longitudinally offset from its adjacent segment(s). Sinusoidal segments 510, 512, 516 will be described in detail below. Sinusoidal segments 108, 116 are as described in the embodiment of FIG. 1 with the sinusoid formed within each segment 108, 116 having first portions 105, 121 respectively, with a gradually increasing amplitude between consecutive turns and longitudinally offset second portions 107, 123, respectively, with a gradually decreasing amplitude between consecutive turns. Adjacent turns of wire 502 within first portion 105 and second portion 123 form an outline of a right trapezoid and adjacent turns of wire 502 within second portion 107 and first portion 121 form an outline of a isosceles trapezoid. First portion 105 and second portion 123 form opposing squared ends 630, 632 of stent 650.

Stent 650, shown in FIG. 6, is formed by wrapping waveform 500 about a mandrel (not shown) starting from either first or second end 504, 506 and proceeding to the opposing end. Welds (not shown) may be used to selectively connect adjacent turns or bends together. First and last sinusoidal segments 108, 116 define opposing end sections of stent 650 with second, third, and fourth sinusoidal segments 510, 512, 514 defining body sections of stent 650. In another embodiment, more or fewer body sections may be used to build on or reduce an overall length of stent 650. First portions 105, 509, 517, 121 and second portions 107, 511, 519, 123 are each of a length L, wherein length L is substantially equal to a circumference of stent 650. In another embodiment, each of first and second portions of sinusoidal segments in accordance herewith may be made longer or shorter in order to increase or decrease an outer/inner diameter of stent 650. Third sinusoidal segment 512 is shown having a length 3·L to be long enough to be wrapped three times around the mandrel without changing pitch angle, similar to a conventionally wrapped helical stent. Segment 512 may have lengths that are less or greater than 3·L to fabricate stents of shorter or greater overall length. In an embodiment, segment 512 may have a length 2·L.

Each of first and fifth sinusoidal segments 108, 116 of waveform 500 is identical to first and fifth sinusoidal segments 108, 116 of waveform 500 and is wrapped around a mandrel in a manner as described in detail above. Further, first portion 509 of second sinusoidal segment 510 and second portion 519 of fourth sinusoidal segment 514 are identical to first portion 109 of second sinusoidal segment 110 and second portion 119 of fourth sinusoidal segment 114 to wrap against first and fifth sinusoidal segments 108, 116 in a manner as described in detail above. Accordingly, these portions and sinusoidal segments are not further described herein except as they relate to additional features of waveform 500 and to forming stent 650.

Second portion 511 of second sinusoidal segment 510 is longitudinally offset from first portion 509 of second sinusoidal segment 510 by a longitudinally extended span of wire 502 that extends from the last turn in first portion 509 to the first turn in second portion 511, with the subsequent consecutive turn of second portion 511 being made to substantially align with a corresponding opposing turn of first portion 509 as similarly described above with reference to corresponding opposing turns 1, 12 of sinusoidal segment 108. When waveform 500 is wound into stent 650, turns of second portion 511 touched by tangent $T_4'$ lie adjacent to turns touched by tangent $T_4$ of first portion 509. Similarly, when waveform 500 is wound into stent 650, second portion 519 of fourth sinusoidal segment 514 is longitudinally offset from first portion 517 of fourth sinusoidal segment 514 such that turns of first portion 517 touched by tangent $T_8$ lie adjacent to turns touched by tangent $T_8'$ of second portion 519. In each of second portion 511 and first portion 517, wire 502 forms a sinusoid that has a constant or uniform amplitude with aligned adjacent turns of wire 502 within each portion 511, 517 forming an outline of a parallelogram (shown dashed).

Third sinusoidal segment 512 is flanked on either end by second portion 511 of second sinusoidal segment 510 and first portion 517 of fourth sinusoidal segment 514 and extends at a wrapping angle $\sigma_1$ therebetween, wherein the wrapping angle is measured from reference line $R_L$ that is perpendicular to longitudinal axis $L_A$ of stent 650. Within third sinusoidal segment 512, wire 502 forms a sinusoid that has a constant or uniform amplitude with adjacent turns of wire 502 forming an outline of a parallelogram (shown dashed). Sinusoidal segment 512 is of a length to be wrapped three times about the mandrel when forming stent 650. Alternatively, the length of segment 512 may be more or less than the exemplary three times the circumference of the wrapping mandrel. The amplitude of third sinusoidal segment 512 is approximately one half of the amplitude of second portion 511 and first portion 517, which have equal amplitudes. When waveform 500 is wound to form stent 650, certain turns of third segment 512 are proximate to turns touched by tangent $T_5$ of second portion 511 and certain other turns of third segment 512 are proximate to turns touched by tangent $T_7$ of first portion 517.

Accordingly, as shown in FIG. 6, stent 650 has alternating and opposing pitch angles $\sigma_1$, $\sigma_2$ due to the sinusoidal patterns of first and fifth segments 108, 116 and a consistent non-alternating pitch angle $\sigma_1$ along a remainder of the body portion of the stent due to the sinusoidal patterns of body segments 510, 512, 514, to provide more consistent physical properties, such as flexibility, along the stent, as described in further detail above regarding stent 250.

While several embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Further, it will be apparent to persons skilled in the relevant art that different features of the various embodiments may be combined with features of other embodiments without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent comprising:
    a wire bent into a waveform having a series of sinusoidal segments, the waveform being wrapped into a hollow cylindrical shape to form the stent, wherein at least one sinusoidal segment of the wire includes:
        a first portion wherein an amplitude between consecutive turns of the wire gradually increases along a length of the first portion from a first amplitude to a second amplitude; and
        a second portion longitudinally offset from the first portion wherein an amplitude between consecutive turns of the wire gradually decreases along a length of the second portion from a third amplitude to a fourth amplitude;
    wherein the second and third amplitudes are substantially equal and wherein a longitudinally extended span of the wire extends from a last turn in the at least one sinusoidal segment first portion to a first turn in the at least one sinusoidal segment second portion with the last turn of the first portion and the first turn of the second portion being consecutive turns of the waveform, and
    wherein the first portion of the at least one sinusoidal segment forms only one complete wrapping of the waveform about a longitudinal axis of the stent and the second portion of the at least one sinusoidal segment forms only one complete wrapping of the waveform about the longitudinal axis of the stent.

2. The stent of claim 1, wherein at least one of the first and second portions has turns of the wire that align in such a manner that a tangent $T_1$ touching the turns is perpendicular to a longitudinal axis $L_A$ of the stent.

3. The stent of claim 2, wherein the turns aligned with the tangent $T_1$ form a squared end of the stent.

4. The stent of claim 2, wherein turns of the wire align in the first portion along the tangent $T_1$ and wherein opposing turns of the wire in the first portion align in such a manner that a tangent $T_2$ touching the opposing turns is at an angle $\sigma L_1$ measured from a reference line $R_L$ that is perpendicular to the longitudinal axis $L_A$ of the stent.

5. The stent of claim 4, wherein turns of the wire in the second portion align in such a manner that a tangent $T_3$ touching the turns is perpendicular to the longitudinal axis $L_A$ of the stent and wherein opposing turns of the wire in the second portion align in such a manner that a tangent $T_2'$ touching the opposing turns is at the angle $\sigma_1$ to the reference line $R_L$.

6. The stent of claim 5, such that opposing turns of the first portion aligned on tangent $T_2$ are positioned along the stent proximate to the opposing turns of the second portion aligned on tangent $T_2'$.

7. The stent of claim 5, wherein the sinusoidal segment has a pitch angle that alternates between being perpendicular to the longitudinal axis of the stent and at the angle $\sigma_1$ to the perpendicular reference line $R_L$.

8. The stent of claim 4, wherein turns of the wire in the second portion align in such a manner that a tangent $T_3$ touching the turns is at an angle $\sigma_2$ measured from the reference line $R_L$ in an opposite angular direction from the angle $\sigma_1$ and wherein opposing turns of the wire in the second portion align in such a manner that a tangent $T_2'$ touching the opposing turns is at the angle $\sigma_1$ to the reference line $R_L$.

9. The stent of claim 8, such that opposing turns of the first portion aligned on tangent $T_2$ are positioned along the stent proximate to the opposing turns of the second portion aligned on tangent $T_2'$.

10. The stent of claim 8, wherein the sinusoidal segment has a pitch angle that alternates between angle $\sigma_1$ and opposing angle $\sigma_2$.

11. A stent comprising:
    a wire bent into a waveform that is wrapped into a hollow cylindrical shape to form the stent, the waveform including a series of sinusoidal segments of the wire;
    wherein each sinusoidal segment includes a first portion having an amplitude between consecutive turns of the wire that gradually increases along a length of the first portion from a first amplitude to a second amplitude and a second portion longitudinally offset from the first portion wherein an amplitude between consecutive turns of the wire gradually decreases along a length of the second portion from a third amplitude to a fourth amplitude, wherein a longitudinally extended span of the wire extends from a last turn in the first portion to a first turn in the second portion with the last turn of the first portion and the first turn of the second portion being consecutive turns of the waveform; and
    wherein each of the first portions of the series of sinusoidal segments forms only one complete wrapping of the waveform about a longitudinal axis of the stent and each of the second portions of the series of sinusoidal segments forms only one complete wrapping of the waveform about the longitudinal axis of the stent.

12. The stent of claim 11, wherein a first sinusoidal segment of the series has turns of the wire in at least one of the first and second portions that align in such a manner that a tangent $T_1$ touching the turns is perpendicular to a longitudinal axis $L_A$ of the stent such that the aligned turns form a squared end of the stent.

13. A stent comprising:
   a wire bent into a waveform that is wrapped into a hollow cylindrical shape to form the stent, the waveform including a series of sinusoidal segments of the wire;
   wherein each sinusoidal segment includes a first portion having an amplitude between consecutive turns of the wire that gradually increases along a length of the first portion from a first amplitude to a second amplitude and a second portion longitudinally offset from the first portion wherein an amplitude between consecutive turns of the wire gradually decreases along a length of the second portion from a third amplitude to a fourth amplitude,
   wherein a longitudinally extended span of the wire extends from a last turn in the sinusoidal segment first portion to a first turn in the sinusoidal segment second portion with a subsequent consecutive turn of the sinusoidal segment second portion being bent at approximately a midpoint between the last turn and a preceding consecutive turn of the sinusoidal segment first portion, and
   wherein each of the sinusoidal segments is longitudinally offset from adjacent sinusoidal segments.

14. The stent of claim 13, wherein adjacent sinusoidal segments of the waveform are longitudinally offset from each other by a longitudinally extended span of the wire.

15. The stent of claim 14, wherein the span of wire extends from a last turn in the second portion of one sinusoidal segment to a first turn in the first portion of an adjacent sinusoidal segment with a subsequent consecutive turn of the wire in the first portion of the adjacent sinusoidal segment being made to substantially align with turns of the wire in the second portion that are aligned in such a manner that a tangent T touching the turns is perpendicular to a longitudinal axis $L_A$ of the stent.

16. The stent of claim 11, wherein a pitch angle of the waveform when wrapped to form the stent alternates between being perpendicular to the longitudinal axis of the stent and at an angle $\sigma_1$ to the perpendicular reference line $R_L$.

17. The stent of claim 11, wherein a pitch angle of the waveform when wrapped to form the stent alternates between an angle $\sigma_1$ measured from a reference line $R_L$ that is perpendicular to a longitudinal axis $L_A$ of the stent and an opposing angle $\sigma_2$ measured from the reference line $R_L$ in an opposite angular direction from angle $\sigma_1$.

\* \* \* \* \*